US00PP18814P2

(12) United States Plant Patent

Korlipara

(10) Patent No.: US PP18,814 P2

(45) Date of Patent: May 13, 2008

(54) *ECHINACEA PURPUREA* PLANT NAMED 'MERLOT'

(50) Latin Name: *Echinacea purpurea*
Varietal Denomination: Merlot

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/705,746

(22) Filed: Feb. 12, 2007

(51) Int. Cl.
*A01H 5/00* (2006.01)

(52) U.S. Cl. ..... Plt./428

(58) Field of Classification Search ..... Plt./263, Plt./428

See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct *Echinacea purpurea* plant named 'Merlot' characterized by its upright, well branched habit, large red purple flowers, multiple flowering stems, and unique deep maroon stems.

1 Drawing Sheet

Botanical denomination: *Echinacea purpurea.*
Variety designation: 'Merlot'.

The present invention relates to a new and distinct cultivar of *Echinacea purpurea* and given the cultivar name 'Merlot'. *Echinacea* is in the family Asteraceae. This new cultivar originated as a seedling from an open pollinated cross between unknown parents.

This new *Echinacea purpurea* cultivar is distinguished by:

1. Large red purple flowers
2. Dark maroon flowering stems
3. Well branched upright habit with multiple flowering stems
4. Fragrance
5. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a 17 months old *Echinacea purpurea* 'Merlot' growing in the ground in full sun in the field in late summer in Canby, Oreg.

DETAILED PLANT DESCRIPTION

The following is a detailed description of the new *Echinacea purpurea* cultivar based on observations of a 17-months-old specimen growing in the ground in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Hardiness.*—USDA Zones 4 to 9.
*Size.*—45 cm wide and 75 cm tall to top of flowers.
*Form.*—Basal clump.
*Vigor.*—Excellent.
*Roots.*—Fibrous, with many downward growing and few laterals, ivory in color, Yellow White 158D, roots develop easily from cuttings from the crown or from crown cuttings.

Stem:

*Type.*—Ascending.
*Size.*—Grows to 75 cm to terminal flower and 1.8 cm wide.
*Internode length.*—2 to 12 cm.
*Surface texture.*—Strigose.
*Color.*—Greyed Purple 187A.

Leaf:

*Type.*—Simple.
*Shape.*—Ovate.
*Arrangement.*—Alternate and basal.
*Blade size.*—Grows to 24 cm long and 12 cm wide.
*Margins.*—Serrate.
*Apex.*—Acuminate.
*Base.*—Attenuate, continuing down petiole.
*Surface texture.*—Strigose.
*Venation.*—Pinnate.
*Color.*—Topside — Yellow Green 147A with the vein Yellow Green 145D. Bottom — Yellow Green 147B with the veins Yellow Green 145C.
*Petiole description.*—Grows to 13 cm long and 1 cm wide if basal leaf, 4 cm long and 4 mm wide if cauline leaf, strigose.
*Petiole color.*—Yellow Green 145B on both sides except in the sun where they are mottled with Greyed Purple 1873 on the top.

Inflorescence:

*Type.*—Long stalked terminal heads.

*Peduncle description.*—Grows to 27 cm where leafless (may have bracts), with diameter growing to 16 mm near the flower head, strigose, branched, with one to five branches, 0 to 6 linear bracts.

*Number of flowering stems per plant in summer.*—1 to 6.

*Bloom time.*—Summer until frost in Canby, Oreg.

Flower:

*Type.*—Perfect, zygomorphic.

*Size.*—Grows to 16 cm wide and 3.5 cm deep as disc enlarges.

*Form.*—Ray florets held horizontally, mature cones are rounded.

*Immature inflorescence.*—3.8 cm wide and 2 cm deep, ray florets held upright and colored Red Purple 59A, disc is colored Greyed Purple 187A.

*Ray florets.*—Without pistil or stamen. Shape: lanceolate with the tip two toothed, entire margins, acute tip. Number: 40 to 57 ray florets per head. Size: grows to 7 cm long, 12 mm wide. Surface texture: glabrous on both sides.

*Disc.*—Shape — convex becoming conic. Size — 4.5 cm to 6.5 cm wide and becoming 3 cm deep with maturity. Florets — 11 mm long, Yellow Green 145B at the base and Brown 200B at the tip, 5 lobed, each flower with one persistent, very stiff bract, 16 mm long, Greyed Purple 185A, which gives the disc color. Pistil — 11 mm long, with an extruding, 2-branched stigma, Greyed Purple 187A, style 5 mm long, ovary 4 mm long and White 155A. Stamen — 5 mm long, extruding from corolla, anthers 2.5 mm long and Brown 200A, pollen Yellow Orange 13A.

*Color.*—Ray florets, topside — Red Purple 70A. Ray florets, bottom side — Red Purple 61A. Disc — Greyed Purple 187A when in bud, then mature to Greyed Purple 185A.

*Involucral bracts.*—In 4 to 5 leafy series, lobes lanceolate in shape, reflexed, strigose, area 5 cm wide, a bract can grow to 2.7 long and 4 mm wide, Yellow Green 147A.

*Bloom period.*—July through October in Canby, Oreg.

*Fragrance.*—Lovely, strong.

Seed: Average number of 11 seeds/head.

*Description.*—4.5 mm long and 2 mm wide, oval, tan, Grey Brown 199D.

*Fertility.*—Low.

Disease and pests: *Echinacea* are susceptible to leaf miners, powdery mildew, bacterial spots, and gray mold. None of these have been observed on plants grown under commercial conditions in Canby, Oreg. No resistance is known.

COMPARISONS TO SIMILAR *ECHINACEA*

Compared to *Echinacea purpurea* 'Ruby Giant', an unpatented plant, the new variety has larger flowers and dark maroon rather than green flowering stems.

Compared to *Echinacea purpurea* 'Fatal Attraction' (U.S. Plant Patent applied for), the new variety has slightly downwardly turned petals with maturity rather than upwardly turned. The new variety is larger growing and has larger flowers. Both have dark flowering stems.

I claim:

1. A new and distinct *Echinacea purpurea* plant as herein illustrated and described.

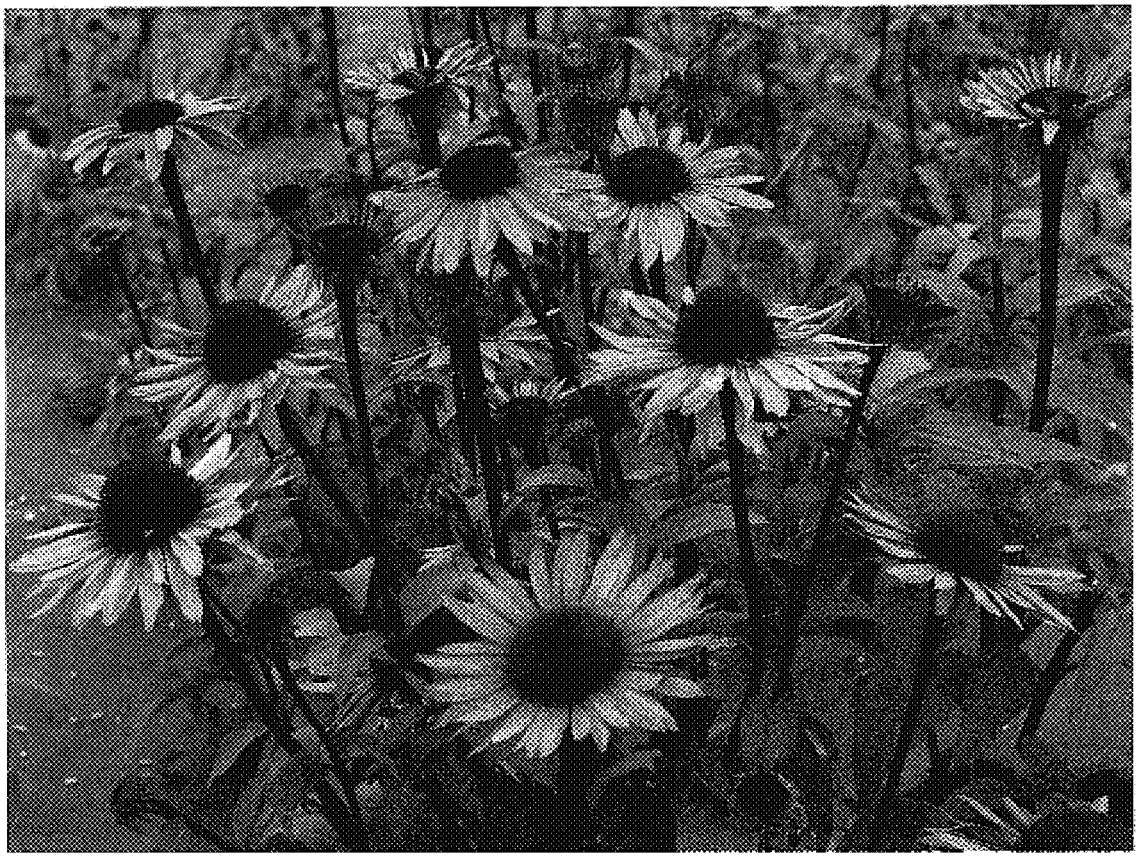

* * * * *